United States Patent
Mascio

(10) Patent No.: US 6,949,115 B2
(45) Date of Patent: Sep. 27, 2005

(54) POLARIZED LIGHT ANALYZER

(75) Inventor: Edward V. Mascio, Huntington Beach, CA (US)

(73) Assignee: Southland Instruments, Inc., Huntington Beach, CA (US)

(*) Notice: Subject to any disclaimer, the term of this patent is extended or adjusted under 35 U.S.C. 154(b) by 0 days.

(21) Appl. No.: 10/684,648

(22) Filed: Oct. 14, 2003

(65) Prior Publication Data

US 2005/0078311 A1 Apr. 14, 2005

(51) Int. Cl.[7] .............................................. A61B 6/03
(52) U.S. Cl. ..................... 607/88; 128/898; 606/133
(58) Field of Search ..................... 128/898; 606/133; 356/369; 607/88

(56) References Cited

U.S. PATENT DOCUMENTS

| | | | | |
|---|---|---|---|---|
| 5,076,696 A | * | 12/1991 | Cohn et al. | 356/369 |
| 5,333,052 A | * | 7/1994 | Finarov | 356/369 |
| 5,450,201 A | * | 9/1995 | Katzir et al. | 356/369 |
| 5,782,851 A | | 7/1998 | Rassman | |
| 5,983,120 A | * | 11/1999 | Groner et al. | 600/310 |
| 5,989,279 A | | 11/1999 | Rassman | |
| 6,572,625 B1 | | 6/2003 | Rassman | |

OTHER PUBLICATIONS

Article on "Application of Physics and Optics to Graft Dissection," 2 pages; IHTI Forhair.com; Copyright 2000–2003 forhair.com; http://www.forhair.com/physicsAndOptics.htm.
Article on "State of the Art Surgical Technique: Follicular Unit Hair Grafting," 7 pages, by Jeffrey S. Epstein, MD; http://www.hairlossresearch.com/ hair_transplant_articles/jepstein_follicular_grafting.htm.
Article on "Frequently Asked Questions on Optics: part 2," 12 pages, Copyright 2003, Edmund Industrial Optics; http://www.edmundoptics.com/techsupport/DisplayArticle.cfm?articleid=285.
Article on "Polarizing Optics Technical Discussion" 4 pages; Oriel Instruments.
Polarization Tutorial, http://www.cvilaser.com/static/tech_polartutor.asp?PrintFriendly=TRUE.

* cited by examiner

Primary Examiner—Henry M Johnson, III
(74) Attorney, Agent, or Firm—Larry K. Roberts; Peter Reitan

(57) ABSTRACT

A follicular dissection system comprises a polarized light source for directing polarized light onto a follicular donor section. An analyzer polarizes image light from the follicular donor section. An optical system provides an image of the follicular donor section from polarized image light from the analyzer.

15 Claims, 5 Drawing Sheets

POLARIZED LIGHT ANALYZER

BACKGROUND OF THE DISCLOSURE

In some hair transplant techniques, including for example micro graft hair transplant techniques, individual follicular units of hair are harvested from a donor region for micro graft transplantation in a recipient region. Follicular unit hair transplantation systems are described, for example, in U.S. Pat. No. 6,572,625 (Rassman), U.S. Pat. No. 5,989,279 (Rassman) and U.S. Pat. No. 5,782,851 (Rassman). Follicular units may be harvested by first removing a section or strip of skin from an area where hair grows. This donor section may then be further dissected and/or sliverized into smaller strips or sections and finally into individual follicular units. A follicular unit is a natural grouping of hairs, from 1 hair up to 4 hairs, most commonly 2 or 3 hairs, which grow together as a group, including a common root sac. The size of individual follicular units may depends on factors including the number of hairs in the follicular unit and the thickness of the individual hairs, with an exemplary range of about 2 um to 4.5 um.

The donor sections or sliverized sections may be viewed under a microscope to identify follicular units for dissection and subsequent transplantation. Magnification of the donor sections make the individual follicular units visible, which may permit a technician to dissect individual follicular units fordissection. If the follicular units are not visualized during dissection, some of the follicular units could be damaged or missed during dissection, thereby reducing the yield from the donor section in terms of the number of transplantable follicular units available for dissection from a given donor section.

In certain donor sections or strips, for example, it may be difficult to distinguish some hairs. Lighter colored hairs may be particularly susceptible to being overlooked or not clearly viewed during dissection. The root sac may also be overlooked or not clearly viewed due to glare or reflected light. As a result, some of the follicular units and/or root sacs in the donor section may not be sufficiently defined or visible in the magnified image of the donor section and may be overlooked and/or damaged during dissection. Overlooking or damaging otherwise transplantable follicular units reduces the number of hairs or follicular units that can be harvested for transplantation from a given donor section.

BRIEF DESCRIPTION OF THE DRAWINGS

Features and advantages of the invention will readily be appreciated by persons skilled in the art from the following detailed description of an exemplary embodiment thereof, as illustrated in the accompanying drawings, in which.

DETAILED DESCRIPTION OF THE DISCLOSURE

Figure 1:
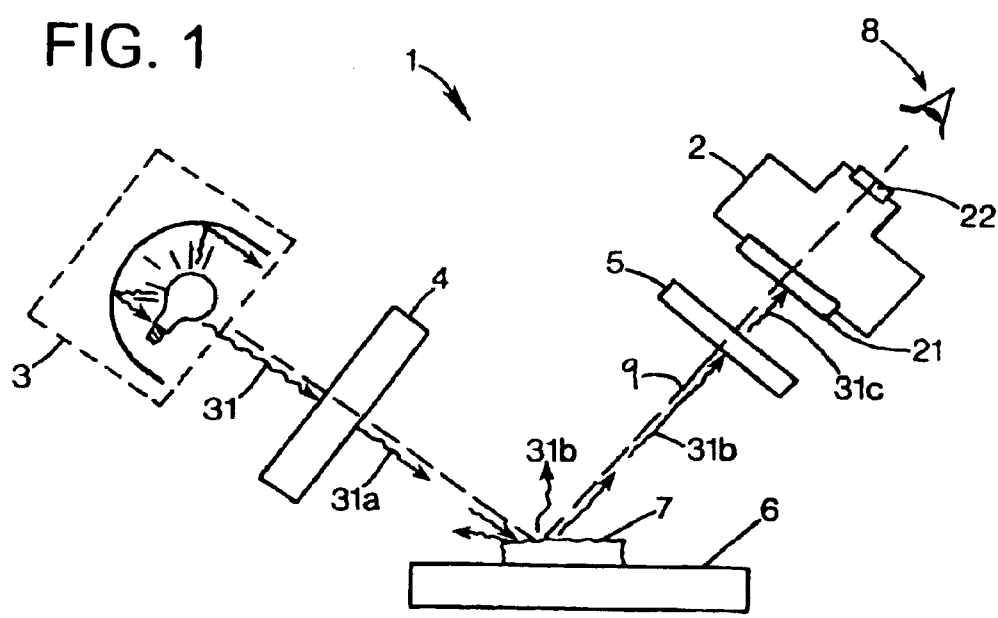
FIG. 1 is a simplified diagram of a microscopic viewing system.

In the following detailed description and in the several figures of the drawing, like elements are identified with like reference numerals.

FIG. 1 shows a simplified diagram of a viewing system 1 which may be a part of a follicular dissection station or system. The viewing system 1 includes an optical magnifying system 2, a light source 3, a source polarizer 4 and an image polarizer or analyzer 5. The image analyzer and source polarizer may be polarizing filters and may be either linear or circular polarizers, such as, for example, rotating polarizers including Meiji Techno part nos. MA 550, MA 550/05 or MA 550/12 and/or mounted polarizers available from Edmund Scientific. In an exemplary embodiment, the optical magnifying system may be a microscope, which may be a stereo microscope. In other exemplary embodiments, the optical magnifying system may comprise a lens system for an image capture device, such as a video camera, and may comprise an image processor for digitally magnifying a image data.

Figure 7:
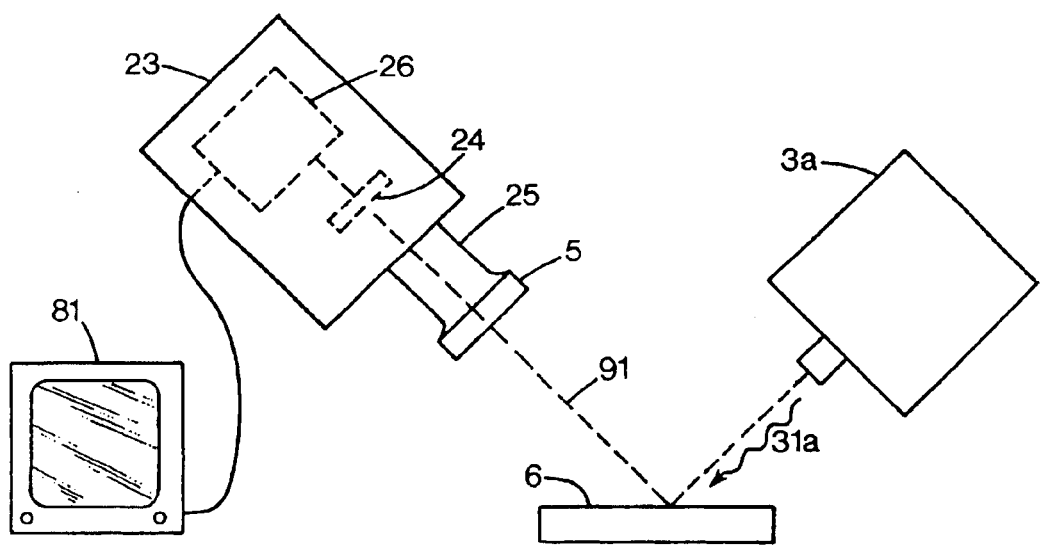
FIG. 7 illustrates an exemplary embodiment of a follicular dissection system with an image capture device and a polarized light source.

An optical path 9 extends from the light source 3 to a viewer 8. Light 31 from the light source is directed, directly or indirectly, along the optical path 9 from the light source 3. The light 31 passes through the source polarizer 4, which allows polarized light 31a to pass. The polarized light 31a is directed along the optical path 9 to an object 7 on a viewing surface 6. Reflected light 31b is reflected from the object 7 and directed along the optical path 9 through the image analyzer 5. The analyzer 5 permits polarized light 31c to pass. The polarized light 31c is directed along the optical path 9 to the microscope 2. The light 31c may be collected by a collector lens 21, guided further along the optical path 9 through, for example, a microscope, and out an eyepiece lens 22. The optical magnifying system 2 creates a magnified image of the object that may be viewed, in the case of a microscope, by a viewer 8 looking into the eyepiece lens 22 of a properly adjusted microscope 2. In the case of a stereo microscope, the microscope may have two eyepieces, each one having an eyepiece lens 22. In the case of an image capture device, the image may be viewed, for example, on a video screen (see FIG. 7).

In the exemplary embodiment of FIG. 1, the analyzer 5 is placed between the object to be viewed and the microscope 2. In alternative, exemplary embodiments, the analyzer may be placed anywhere along the optical path 9 between the object 7 and the viewer 8. For example, the analyzer could be placed within an optical magnifying system 2, for example, between the collector lens 21 and the eyepiece 22 of a microscope, or could be placed between the magnifying system 2 and the viewer 8. In an exemplary embodiment with a stereo microscope, two analyzers 5 may be placed, one each between each one of two eyepiece lenses 22 and the viewer. If the optical path 9 splits within the microscope at a position between the collector lens 21 and the eyepiece lenses 22, two analyzers could be placed one each in each branch of the split optical path 9 before each of two eyepiece lenses 22 of a stereo microscope. In the alternative, an analyzer could be placed in the optical path 9 before a split of the optical path in a stereo microscope.

In an exemplary embodiment, one of or both of the source polarizer 4 and analyzer or analyzers 5 may be rotatable about the optical path 9. When adjusting the viewing system for viewing an object, rotating the source polarizer 4 and or image analyzer 5 may bring the relative position of the axis of polarization of the analyzer, with respect to the polarization of some of light from the object, to a position which creates a desired degree of extinction. In the case of a stereo microscope with two analyzers 5, both analyzers may be adjusted to provide a desirable degree of extinction. In the alternative, the source polarizer is rotated to provide the desired amount of extinction of the polarized light. In an exemplary embodiment, two analyzers 5 in two branches of a split optical path 9 of a stereo microscope could be oriented along the same axis of polarization when adjusted to provide the desired degree of extinction.

In an exemplary embodiment, the desired degree of extinction is achieved where the glare and/or reflective shine that would otherwise make it difficult to discern certain details in a magnified image are sufficiently reduced so that those details are more defined and/or more discernable in the image viewed through the microscope 2. For example, where a microscopic viewing system is used for viewing and dissection of a follicular hair transplant donor section (FIG. 2), reflected light and glare may make it difficult to distinguish or discern some hairs, follicular units and/or root sacs in the microscopic image. Lighter colored hairs, for example, may be particular susceptible to being difficult to discern from among darker hairs in a microscopic image. When the donor site is viewed through an exemplary viewing system with a source polarizer 4 and an analyzer 5 adjusted to provide the desired degree of extinction, hairs, follicular units of hairs and root sacs or root balls may be more defined and more easily distinguishable in the image.

In the exemplary embodiment of FIG. 1, the desired position or positions of the analyzer 5 and/or the polarizer 4 may be chosen to permit sufficient light through to make the details of the object 7 being viewed visible while reducing the amount of glare and/or making the otherwise-difficult-to-see hairs more distinct. To provide sufficient light under desirable extinction conditions, the light source may have a controller for adjusting the intensity of the light to a desired level of light.

Viewing an object 7 with the polarizer 4 and/or analyzer 5 in the desired position may also provide images from light reflecting from deeper in the sample. For example, in the case of viewing follicular units in a donor section of human skin, the desired position may make follicular unit root sacs or root balls more visible or better defined, even where the root sac is below the skin. This may enable a technician to make cleaner cuts so as not to damage the root sac or follicular unit when slivering or dissecting a donor sample for transplantation.

Figure 2:
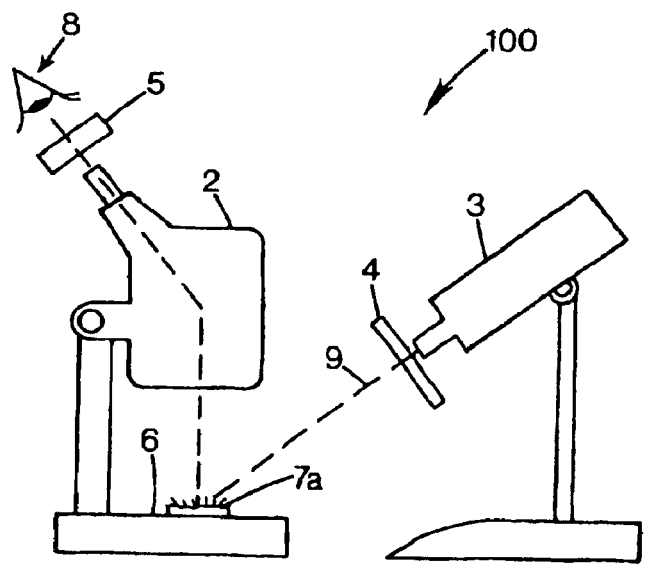
FIG. 2 illustrates an exemplary embodiment of a follicular dissection system with a microscopic viewing system having a stand-alone light source.
Figure 3:
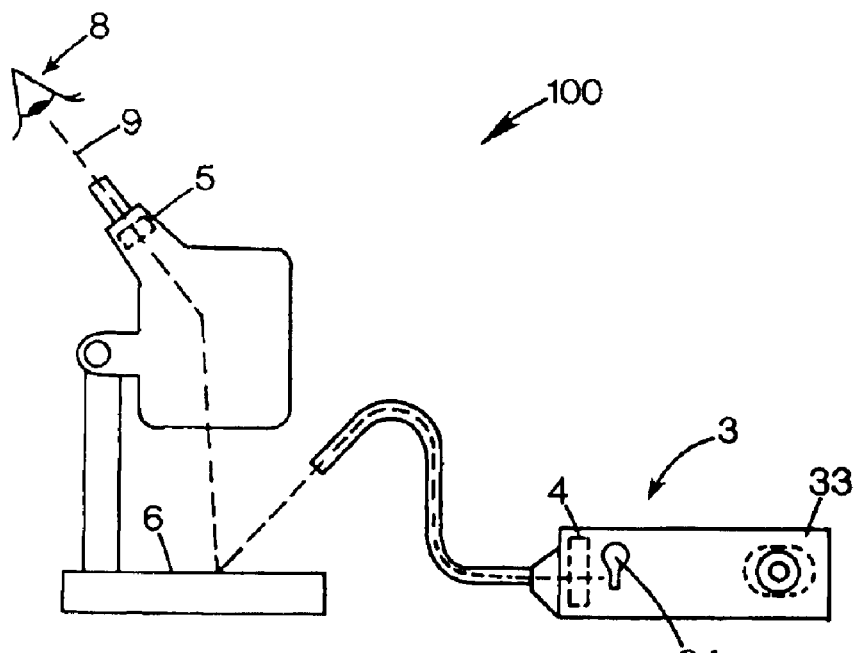
FIG. 3 illustrates an exemplary embodiment of a follicular dissection system with a microscopic viewing system having a stand-alone fiber optic light source.

FIG. 2 illustrates an exemplary embodiment of a follicular dissection station 100. The follicular dissection station 100 may comprise a stand-alone light source 3, a source polarizer 4, a viewing surface 6, an analyzer 5 and a microscope 2. The light source 3 may be an incandescent light source, a flourescent light source, a halogen light source or other source of light. The light source may be selected to provide sufficient illumination of the object to be viewed when the polarizer 4 or the analyzer 5 are adjusted to the desired degree of extinction. The light source may be, for example, a 6v, 20 W halogen light or a 150 W or 250 W halogen light source. In the exemplary embodiment of FIG. 3, the light source 3 is a fiber-optic illuminator. The fiber-optic illuminator 3 may have a 150 W or 250 W, variable intensity halogen lamp 34 with a variable intensity controller 33 and coupled to one or more light pipes 32. The light pipes 32 may have lenses mounted at the ends for focusing light leaving the light pipes onto an object being viewed on the viewing surface 6. In the exemplary embodiment of FIG. 3, a source polarizer is located in the optical path 9 between the lamp 34 and the light pipes 32. In an alternate embodiment (not shown), the source polarizer may be rotatably mounted at the exit end of the light pipe or pipes 32. The light pipes 32 may be self-supporting or flexible. Exemplary illuminators are available, for example, from Techniquip Corporation.

With reference to FIG. 2, a technician may sliverize or dissect a donor section 7a for hair transplantation while viewing a microscopic image of the donor section on the viewing surface 6. It may be desirable to design the optics of the microscope to permit sufficient space or working distance between the microscope and the viewing surface to permit a technician to perform dissection or sliverization of a donor section 7a. In an exemplary embodiment, a stereo microscope 2 may provide low magnification, for example between 5x–50x magnification, while providing adequate working distance to perform dissection or sliverization of a donor section.

In the exemplary embodiment shown in FIG. 2, the source polarizer 4 is shown in a position at the output of the light source 3. In alternate embodiments, the source polarizer may be placed anywhere between the light source and the viewing surface 6, such that the light incident on an object to be viewed is polarized light. In the case of a fiber optic illuminator, the polarizer may be placed between the light source and the entrance to the light pipes or at the end of the light pipes. In this exemplary embodiment, the analyzer 5 is shown at a location between the microscope 2 and the viewer 8. In alternative, exemplary embodiments, the polarizer 4 could be placed anywhere along the optical path 9, between the viewing surface and the viewer, including, for example, within the microscope 2 or between the viewing surface 6 and the microscope 2.

In an exemplary embodiment, an existing follicular dissection station 100 may be modified by mounting an appropriately placed source polarizer 4 and an appropriately placed image analyzer 5, such that the polarizer 4 and/or analyzer 5 may be rotated to create a desirable amount of extinction to provide more definition of certain features in a magnified image of an object 7a. For example, an existing follicular dissection station could be used in conjunction with an analyzer 5 placed either between the follicular viewing surface 6 and the microscope 2 or between the microscope 2 and the viewer 8 and with a polarizer 4 between the light source 3 and the viewing surface 6. For example, an image analyzer could be rotatably mounted at the entrance to the microscope (not shown). The analyzer may be rotatably mounted on a cap which may be thread-mounted to the entrance to the microscope. In the embodiment of FIG. 2, the analyzer 5 is rotatably placed at the exit of the microscope. The analyzer 5 may be rotatably mounted on a cap which may be thread-mounted at the exit of the eyepiece of the microscope.

Figure 4:
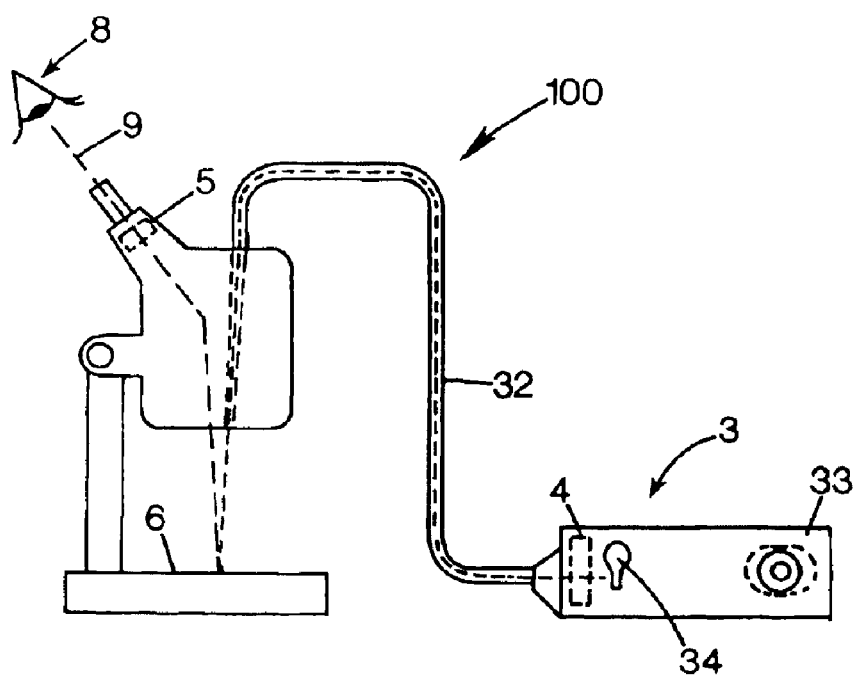
FIG. 4 illustrates an exemplary embodiment of a follicular dissection system with a microscopic viewing system having an integrated fiber-optic light source.

FIG. 4 illustrates an exemplary embodiment of a follicular dissection station 1 with an integrated, fiber-optic light source 3. The light source may be, for example, a 250 W fiber-optic illuminator. The light source 3 is coupled to the microscope through a fiber optic light pipe 32. The fiber optic light pipe 32 is integrally coupled with the microscope 2 and arranged so that light from the light source 3 is directed onto the viewing surface 6 from an angle at or near the angle at which the microscope optics view the viewing surface 6. The source polarizer 4 may be placed in a position along the optical path 9 between the light pipe (as shown) and the lamp 34 within the illuminator 3 at the beginning of the fiber optics 32 or integral with the microscope at or toward the end of the fiber optics (not shown). The fiber optics 32 may be arranged so that the optical path is directed down onto the viewing surface and the object to be viewed from approximately the same direction as the viewing angle. The illuminator 3 may include a controller 33 to adjust the intensity. The illuminator 3 and/or fiber optics 32 may be arranged as an integral part of a follicular dissection station 100. In an alternate embodiment, the follicular dissection station may comprise more than one light pipe.

Figure 5:
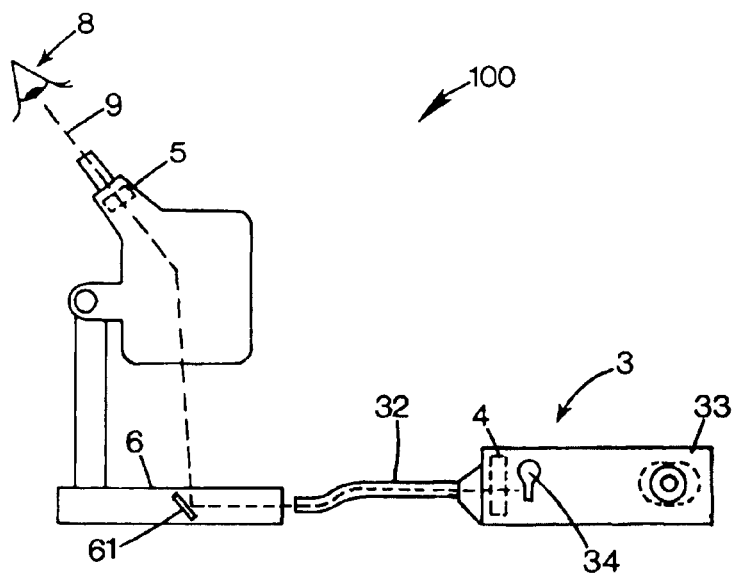
FIG. 5 illustrates an exemplary embodiment of a follicular dissection system with a microscopic viewing system with through lighting.

In a further exemplary embodiment illustrated in FIG. 5, light from a light source 3 may shine up from below the viewing surface 6 and through an object being imaged. The light may be from a light source 3 shining directly up toward the microscope 2 or may be directed, for example by fiber optics 32 and/or a mirror 61 or mirrors, to pass up from below an object to a microscope 2. The source polarizer 4 is arranged in the optical path 9 between an illuminator 34 and the object. The image analyzer 5 is placed in the optical path 9 between the object 5 and the viewer 8.

Figure 6A:
FIG. 6A illustrates an exemplary image of human skin and hair viewed through a microscopic viewing system without a source polarizer and an analyzer.
Figure 6B:
FIG. 6B illustrates an exemplary image of human skin and hair viewed through a microscopic viewing system with a source polarizer and an analyzer adjusted to a desired degree of extinction.

FIGS. 6A and 6B illustrate exemplary views of human skin with hair viewed through a microscope. FIG. 6A illustrates how glare and/or reflected light may obscure, or render less-visible, lighter colored hair 15. FIG. 6B illustrates a view of the same patch of human skin when viewed through a microscope using a source polarizer and an image polarizer. The lighter colored hair 15 is more defined and stands out more clearly among the darker colored hairs than in FIG. 6A.

The embodiments discussed above and illustrated in FIGS. 1–5 show the viewer 8 as a human eye. In alternate exemplary embodiments, the viewer 8 may comprise a video camera, camera or other image capturing device. An image capturing device may generate a signal which can be digitized or otherwise stored on a recording medium or computer memory device and/or be sent to an imaging or viewing device, such as a television screen, projector, computer monitor or the like for viewing. The images can be viewed in real time or recorded or stored for later viewing. The image capturing device can be placed in a position to receive and create an image for display from the light from the sample.

In an exemplary embodiment, the viewing system may comprise a camera, video camera and/or a lens system for a video capturing device. The video capture device may or may not comprise magnification optics. The image created captured by the device may be magnified by optics prior to being captured or may be magnified electronically or digitally by a processor or may be magnified by a combination of the two. The image analyzer 5 may be placed anywhere in the optical path 9 between the object being viewed and the surface where the image is captured. In the exemplary embodiment of FIG. 7, a polarized light source 3a directs polarized light 31a toward an object on a viewing surface 6. The polarized light source may comprise a light source and a source polarizer or may comprise any other source of polarized light 31a. The image analyzer 5 is mounted at the optical entrance to the lens system 25 of a video capture device 23. Light from the object being viewed is captured on a video capture surface 24. The video capture surface may be a CCD array. A video processor 26 creates a signal responsive to the image. The processor 26 may process and further magnify the image. The video capture device 23 is coupled to a viewer 81. The viewer may comprise a television, computer monitor, projector or other viewing device which creates an image responsive to the signal.

It is understood that the above-described embodiments are merely illustrative of the possible specific embodiments which may represent principles of the present invention. Other arrangements may readily be devised in accordance with these principles by those skilled in the art without departing from the scope and spirit of the invention.

What is claimed is:

1. A method of enhancing the visibility of follicular donor sections comprising:

directing polarized light onto a follicular donor section;

directing image light from the follicular donor section through an analyzer, thereby polarizing the image light;

creating an image from the polarized image light.

2. The method of claim 1, further comprising rotating the analyzer to achieve a desired degree of extinction.

3. The method of claim 1, wherein directing polarized light onto a follicular donor section comprises directing light from a light source through a polarizer and onto a follicular donor section.

4. The method of claim 3, further comprising rotating one of the analyzer or the polarizer to achieve a desired degree of extinction.

5. The method of claim 1, wherein the light source is a fiber optic light source.

6. The method of claim 1, wherein the light source is coupled integrally with a microscope.

7. The method of claim 1, further comprising controlling the intensity of the light source.

8. The method of claim 1, further comprising magnifying the image.

9. The method of claim 8, wherein magnifying the image comprises directing image light through a microscope.

10. The method of claim 8, wherein magnifying the image comprises directing image light to an image capture device.

11. The method of claim 10, wherein the image capture device comprises magnifying optics.

12. The method of claim 10, wherein the image capture device comprises a controller and magnifying the image further comprises digitally magnifying the image.

13. A method of dissecting a hair transplant donor section, comprising:

directing polarized light onto the donor section;

directing image light from the donor section through an analyzer, thereby polarizing the light reflected from the donor section;

directing the image light from the object to a microscope to create an image of the donor section;

viewing the image; and dissecting the donor section responsive to the image.

14. The method of claim 13, further comprising rotating the analyzer to achieve a desired degree of extinction.

15. The method of claim 14, wherein achieving the desired degree of extinction comprises enhancing the visibility of light colored hair.

* * * * *